(12) United States Patent
Halperin

(10) Patent No.: US 6,976,488 B2
(45) Date of Patent: Dec. 20, 2005

(54) MEDICATION BYPASS HEAT AND MOISTURE EXCHANGE UNIT

(75) Inventor: Scott Halperin, Orange, CA (US)

(73) Assignee: Allegiance Corporation, McGaw Park, IL (US)

(*) Notice: Subject to any disclaimer, the term of this patent is extended or adjusted under 35 U.S.C. 154(b) by 147 days.

(21) Appl. No.: 10/282,418

(22) Filed: Oct. 30, 2002

(65) Prior Publication Data

US 2004/0084046 A1 May 6, 2004

(51) Int. Cl.⁷ .................. A62B 18/08; B01D 46/42
(52) U.S. Cl. .................. 128/201.13; 128/204.18; 128/205.12; 128/204.17; 55/314; 55/422
(58) Field of Search ............... 128/201.13, 200.14, 128/200.23, 203.15, 204.17, 204.18, 205.11, 128/205.12, 205.27, 910, 911; 604/58; 165/4, 165/6, 8, 57, 58, 66; 55/312, 314, 422

(56) References Cited

U.S. PATENT DOCUMENTS

| | | | |
|---|---|---|---|
| 4,109,656 A | 8/1978 | Goethel et al. | 128/266 |
| 4,649,911 A | 3/1987 | Knight et al. | 128/200.21 |
| 4,936,297 A | 6/1990 | Greiff et al. | 128/203.25 |
| 5,025,806 A | 6/1991 | Palmer et al. | 128/203.12 |
| 5,078,131 A | 1/1992 | Foley | 128/203.15 |
| 5,159,924 A | 11/1992 | Cegielski et al. | 128/203.12 |
| 5,237,990 A | 8/1993 | Psaros et al. | 128/204.21 |
| 5,323,772 A | 6/1994 | Linden et al. | 128/204.23 |
| 5,357,946 A | 10/1994 | Kee et al. | 128/200.24 |
| 5,373,842 A | 12/1994 | Olsson et al. | 128/204.21 |
| 5,546,930 A | 8/1996 | Wikefeldt | 128/200.21 |
| 5,603,314 A | 2/1997 | Bono | 128/200.21 |
| 5,666,946 A | 9/1997 | Langenback | 128/200.16 |
| 5,692,498 A | 12/1997 | Lurie et al. | 128/205.24 |
| 5,694,922 A | 12/1997 | Palmer | 128/202.27 |
| 5,992,413 A | 11/1999 | Martin, Jr. et al. | 128/201.13 |
| 6,095,135 A | 8/2000 | Clawson et al. | 128/201.13 |
| 6,105,576 A | 8/2000 | Clawson et al. | 128/205.12 |
| 6,415,788 B1 * | 7/2002 | Clawson et al. | 128/201.13 |
| 6,550,476 B1 * | 4/2003 | Ryder | 128/201.13 |

* cited by examiner

Primary Examiner—Mital Patel
(74) Attorney, Agent, or Firm—Michael D. Steffensmeier

(57) ABSTRACT

The present invention provides a heat and moisture exchange (HME) unit that includes a housing having a fibrous media in the housing that is designed to absorb and retain moisture and heat from exhaled air passing through the housing. The HME unit is designed to transfer the moisture and heat to inhaled air passing through the HME unit. The HME unit has an internal bypass in the housing to enable air to pass through the heat HME unit without passing through the fibrous media. The present invention also provides a breathing circuit that includes a medication bypass HME unit, a medication treatment device and a ventilator that is connected in a closed system.

12 Claims, 14 Drawing Sheets

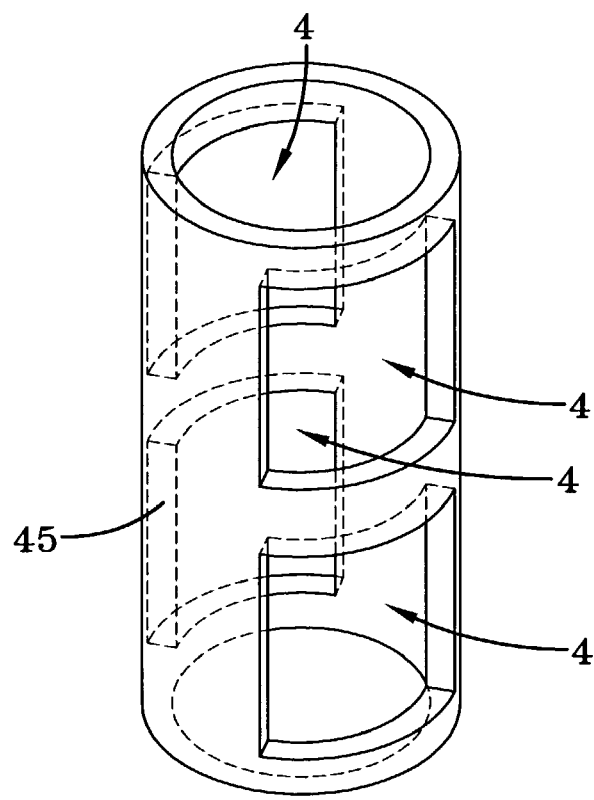
FIG-4
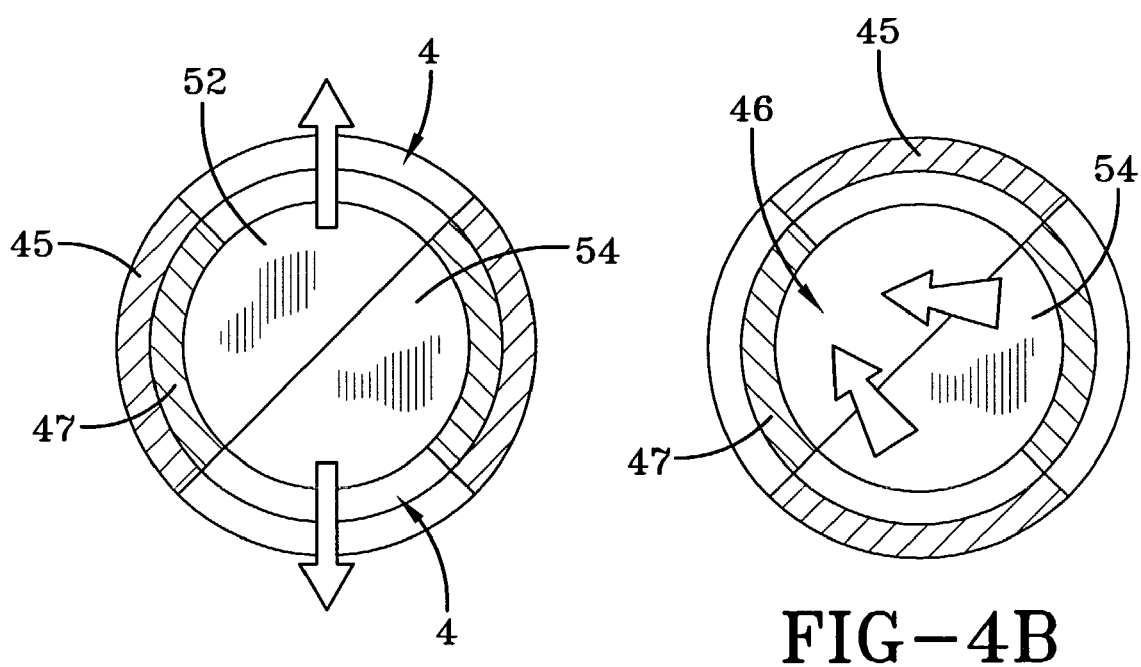
FIG-4A
FIG-4B

MEDICATION BYPASS HEAT AND MOISTURE EXCHANGE UNIT

FIELD OF THE INVENTION

The present invention relates to a heat and moisture exchange (HME) unit that is used in conjunction with a breathing circuit and a ventilator in order to provide a patient with breathing assistance. More specifically, the HME unit has an internal bypass inside of its housing to enable air to pass through the HME unit without passing through the fibrous heat and moisture media in the HME unit.

BACKGROUND AND SUMMARY OF THE INVENTION

The use of ventilators and breathing circuits to assist in patient breathing is well known in the art. The ventilator and breathing circuit provide mechanical assistance to patients who are having difficulty breathing on their own. During surgery and other medical procedures, the patient is often connected to a ventilator to provide respiratory gases to the patient. One disadvantage of the use of such breathing circuits is that the air that is delivered to the patient's lungs does not provide the appropriate humidity to the lungs. In addition, the air that is delivered from a breathing circuit to the patient's lungs is not at the appropriate temperature.

In order to provide for proper humidity and temperature of the air, the use of an HME unit in the breathing circuit is used. Such HME units generally consist of a housing that contains a layer of flexible, fibrous, gas-permeable media or material. This media has the capacity to retain moisture and heat from the air that is exhaled from the patient's lungs and then transfer the captured moisture and heat to the inhaled air when the patient is inhaling. This fibrous material or media in the HME unit may be made of foam or paper or other suitable materials that are untreated or treated with hygroscopic material.

While the use of such HME units has addressed the problem of the heat and humidity of the air being provided to the patient in a breathing circuit, use of the HME unit has its own drawbacks. When administering medicine to a patient by use of a nebulizer or other treatment device, the fibrous media in the heat and moisture exchange unit can become clogged with the droplets of liquid medication that are provided from the nebulizer. Thus, to deliver medication via the nebulizer or other treatment device when a breathing circuit is in use, the HME unit must be removed from the circuit or from the nebulized air flow. Removal of the HME unit from the circuit takes the time of a health care provider that is better spent administering to the patient and opens the breathing circuit to the ambient air with possible contaminants.

It is highly desirable when using a breathing circuit to maintain the breathing circuit as a closed system. This is desirable because maintaining a closed system minimizes the exposure of the patient to bacteria and other contaminants, thus reducing the risk of the patient becoming infected. However, if nebulized medicine is to be administered to a patient in a breathing circuit with an HME unit and the HME unit is removed, the closed breathing circuit is breached and the breathing circuit is exposed to ambient air. This not only increases the risk of infection but also leaves the patient with a depressurized breathing circuit during the time that the closed breathing circuit is breached.

U.S. Pat. No. 6,095,135 (Clawson et al.) discloses a fairly complicated apparatus for heating and humidifying respiratory gases with a fitting joined to both a housing and tracheal tube device as well as a fitting closure assembly that moves to open and close a second end opening of the fitting. This patent discloses a bypass line or tube that is external to and outside of the HME portion of the apparatus. A nebulizer or other treatment device can be connected to this external bypass line. The fitting closure assembly is a valve that moves to direct air flow through the external bypass line so that the air does not pass through the housing of the HME unit. Some of the drawbacks of this invention are that it requires multiple components, including valves, fittings and a separate external bypass line outside of the housing of the HME unit in order to operate.

It is desirable to have an HME unit with self-contained internal bypass that will allow medicated air from a nebulizer to flow through the housing of the HME unit, but flow past the fibrous material in the HME unit and to the patient without requiring complicated valves and external bypass tubes. It is also desirable to have an HME unit for a breathing circuit that allows for medication to be delivered to the patient via a nebulizer without unduly consuming the time of the health care provider while maintaining the closed system of the breathing circuit.

The present invention meets these needs. The present invention provides an HME unit having a housing including a fibrous media and an internal bypass in the housing that enables air to flow past the fibrous media when desired (e.g., when using a nebulizer to provide medication to a patient). The present invention also provides a breathing circuit that includes an HME unit, a medication treatment device such as a nebulizer, and a ventilator. The respirator, the medication treatment device and the HME unit are connected in a closed system.

Various objects and advantages of the present invention will become apparent from the following detailed description when viewed in conjunction with the accompanying drawings, which set forth certain embodiments of the invention.

BRIEF DESCRIPTION OF THE DRAWINGS

FIG. 4 is a perspective view of a portion of the HME unit of FIG. 3 in accordance with the present invention.

FIGS. 4A and 4B are cross-sectional views of the HME unit of FIG. 3 in accordance with the present invention.

DETAILED DESCRIPTION OF THE PREFERRED EMBODIMENTS

The detailed embodiments of the present invention are disclosed herein. It should be understood, however, that the enclosed embodiments are merely exemplary of the invention, which may be embodied in various forms. Therefore, the details disclosed herein are not to be interpreted as limiting, but merely as a basis for teaching one skilled in the art how to make and/or use the invention.

Figure 1:
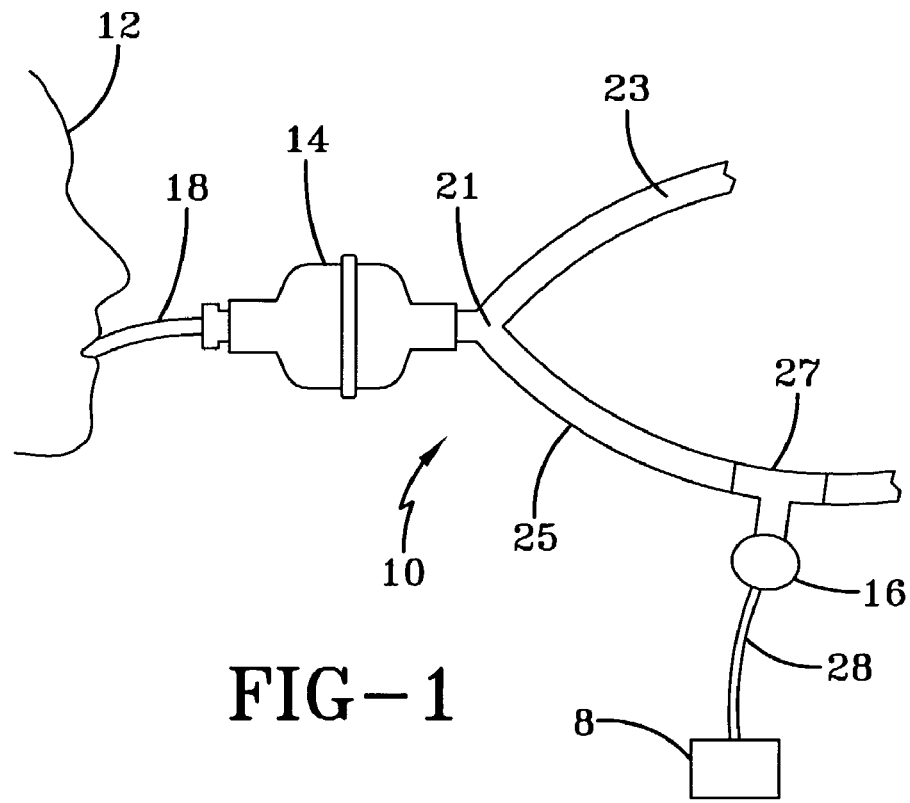
FIG. 1 shows a breathing circuit using an HME unit and a nebulizer in accordance with the present invention.

Referring to the drawings, FIG. 1 shows a dual limb breathing circuit 10 having a number of flexible tubing segments that are connected in between a patient 12, the HME unit 14, the nebulizer 16, a source of pressurized air 8, and a ventilator (not shown).

In particular, a patient tube 18 is provided that connects the patient 12 to the HME unit 14. The end of the patient tube 18 that interfaces with the patient 12 can be an endotracheal tube that extends through the patient's mouth and throat and into the patient's lungs. It also may be connected to a tracheostomy tube (item 119 in FIG. 2) that provides air to the patient's throat and thereby to the patient's lungs. Extending on the opposite side of the HME unit 14 is a Y-connector 21. The Y-connector 21 may be connected to the two flexible tubes. The first tube, the exhalation tube 23, allows exhaled air to leave the breathing circuit 10. The second tube, the nebulizer tube 25, is connected to the nebulizer 16. The nebulizer 16 is connected to the nebulizer tube 25 through a T-connector 27. The T-connector 27 is connected at the end opposite of the nebulizer tube 25 to a ventilator (not shown). The nebulizer 16 is also connected to a source of pressurized air 8 through an air tube 28.

Figure 2:
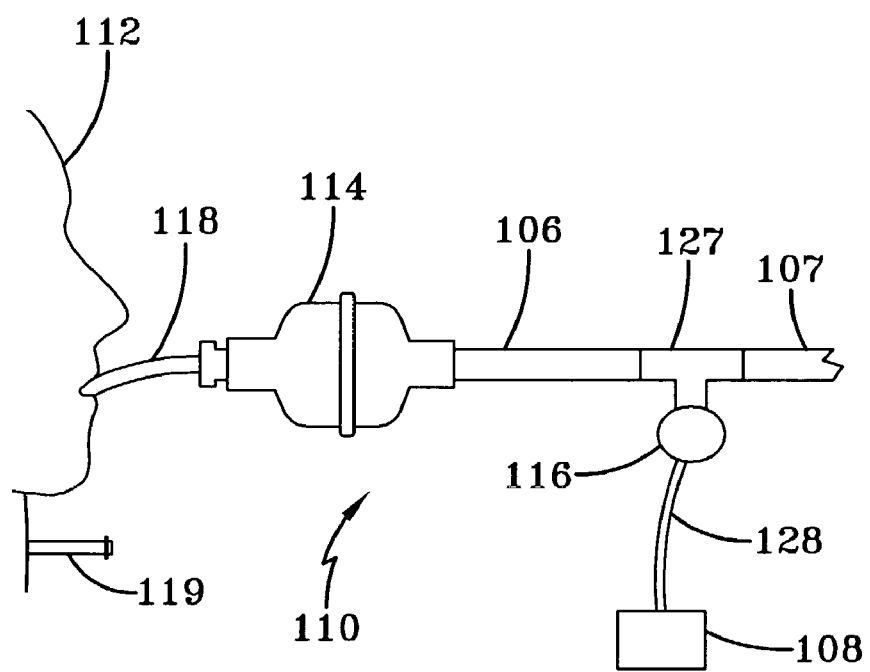
FIG. 2 shows a breathing circuit using an HME unit and a nebulizer in accordance with the present invention.

FIG. 2 shows a single limb breathing circuit 110 that includes a number of flexible tubing segments that are connected between a patient 112, the HME unit 114, the nebulizer 116, a source of pressurized air 108, and a ventilator (not shown). There are similarities between the single limb breathing circuit 110 and the dual limb breathing circuit 10, but for the single limb breathing circuit 110, the ventilator delivers gas through tube 107, the nebulizer tee 127, the tube 106, through the HME unit 114 through the endotracheal tube 118 and to the patient 112. The patient 112 exhales out of these same tubes and the HME unit 114 and through tube 107. Single limb breathing circuit 110 may also be connected to a tracheostomy tube 119, if necessary.

The present invention contemplates use of various types of nebulizers 16. In one such type of nebulizer 16, medication is provided which has been reconstituted with sterile water and placed in a reservoir provided in the nebulizer 16. Pressurized gas is provided to the nebulizer 16 which is blown across an atomizer in the nebulizer 16. The force of the gas over the atomizer pulls the medicated liquid from the medication reservoir up along the sides of the nebulizer 16 in a capillary action to provide a stream of the medicated liquid at the atomizer. When the medicated liquid hits the stream of forced air at the atomizer, the liquid is atomized into a multiplicity of small droplets. The force of the air propels this now nebulized mixture of air and medicated liquid into the breathing circuit and to the patient, where the medication is provided to the patient's lungs. Use of administration of medication in this procedure has been found to be highly effective in providing the medication through the lungs to the patient. Metered dose inhalers could also be used to provide medication in the air to the patient.

Figure 3:
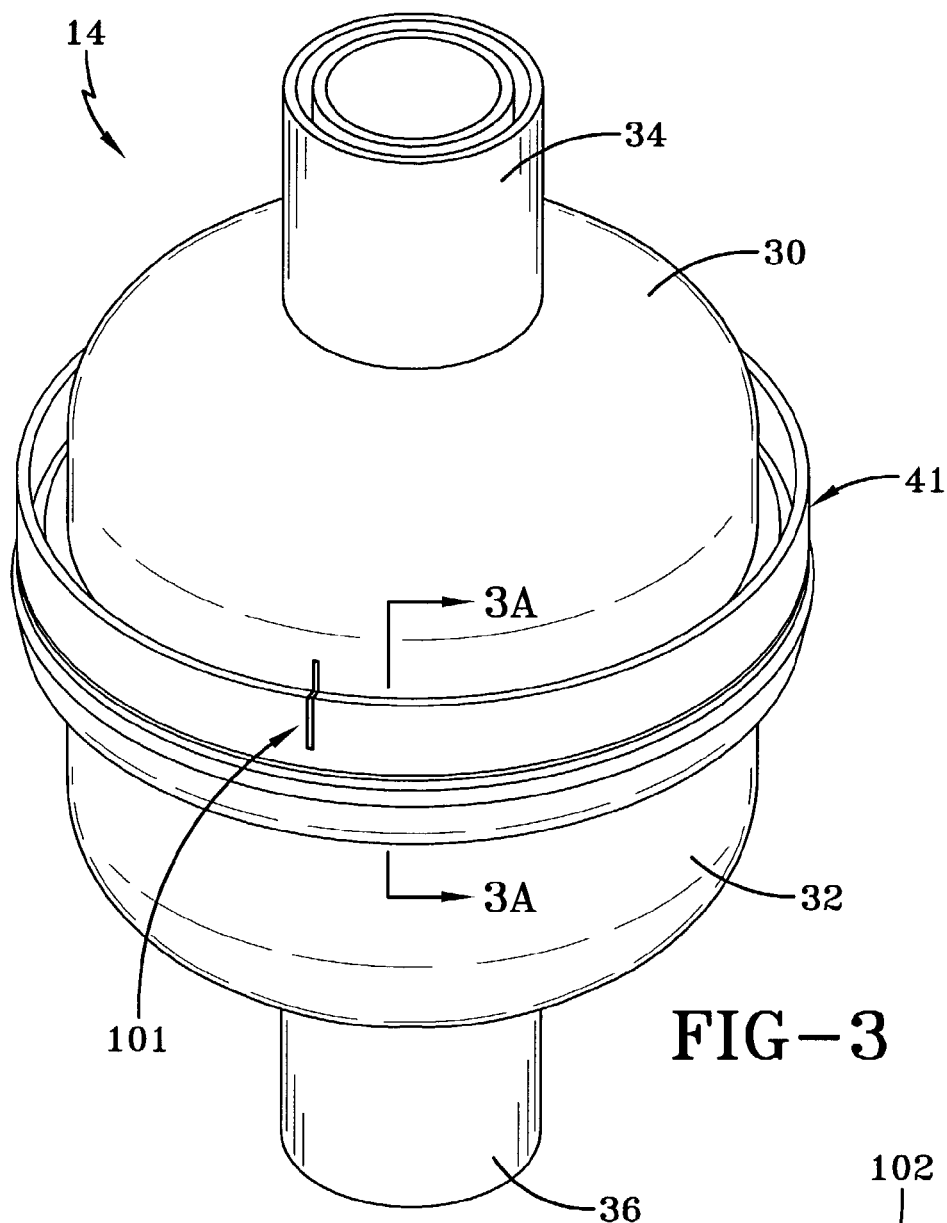
FIG. 3 is a perspective view of an HME unit made in accordance with the present invention.
Figure 3A:
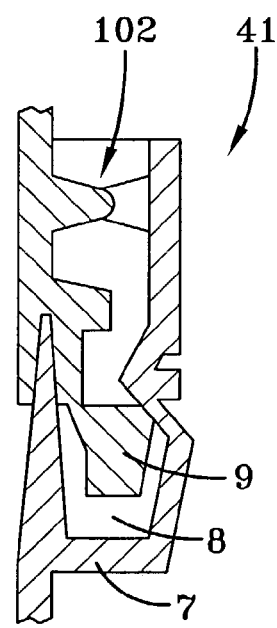
FIG. 3A is a cross-sectional view of the interlocking connection of the HME unit of FIG. 3 in accordance with the present invention.

FIG. 3 shows a perspective view of an HME 14 made in accordance with the present invention. The HME unit 14 includes two cooperating housings, a first HME housing portion 30 and second HME housing portion 32. The first HME housing portion 30 is located adjacent to the Y-connector 21 while the second HME housing portion 32 is located adjacent to the patient tube 18. The end of the first HME housing portion 30 includes a connector 34 that is designed to be secured to the Y-connector. The end of the second HME housing portion 32 includes a connector 36 that is designed to be connected to the patient tube 18. The first HME housing portion 30 and the second HME housing portion 32 include an interlocking connection 41. The interlocking connection 41 connects the first HME housing portion 30 to the second HME housing portion 32 while allowing the first HME housing portion 30 and the second HME housing portion 32 to rotate relative to each other without allowing air to enter into or escape from the HME unit 14. In FIG. 3A, the interlocking connection 41 is shown in a cross-sectional view in which ridge 9 snaps into channel 8 which is formed by lip 7.

Figure 5:
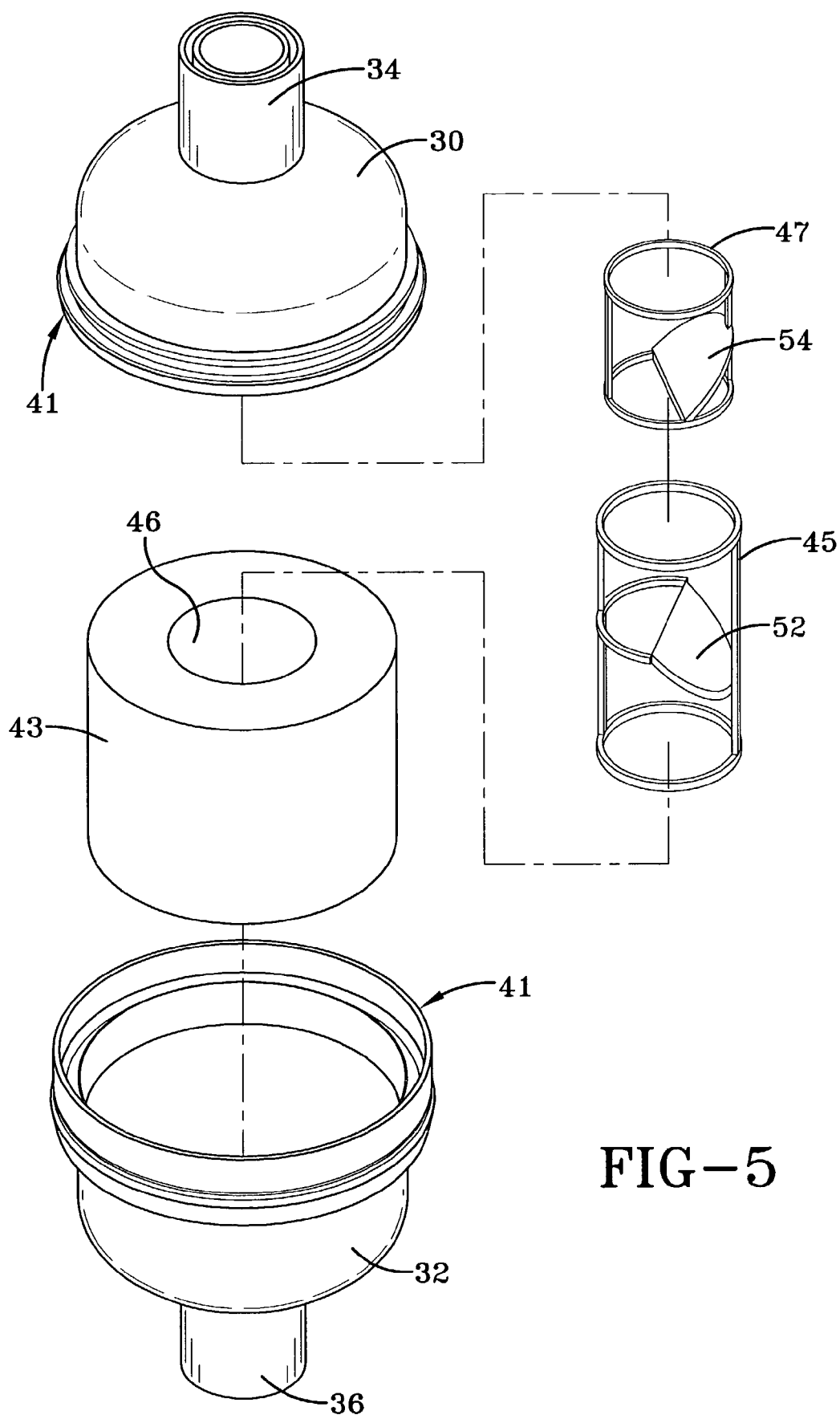
FIG. 5 is an exploded view of the HME unit of FIG. 3 in accordance with the present invention.

Referring to FIG. 5, the bypass 46 is inside of and extends through the HME unit 14 and provides a path through the HME unit 14 that enables air to flow through the bypass 46 without passing through the fibrous media 43. The fibrous media 43 is designed to absorb and retain moisture and heat from exhaled air and then to transfer the retained moisture and heat to air as it is inhaled into the patient's lungs. In the typical HME unit of the prior art, if nebulized air having a multiplicity of microscopic size liquid droplets was directed through the HME unit, these liquid droplets would quickly saturate and clog the fibrous media 43 in the HME unit 14 because there is no bypass. Very little medication would reach the patient unless the HME unit was disconnected and removed from the breathing circuit.

In accordance with the present invention, a bypass 46 is provided through the fibrous media 43 and through the HME unit 14. The bypass 46 that is provided through the fibrous media 43 could be a tunnel or channel through the middle of the material of the fibrous media 43 or there could be an actual tube that extends through the material of the fibrous media 43. In a preferred embodiment of the HME unit 14, the internal bypass 46 includes a first bypass housing 47 and a second bypass housing 45. The first bypass housing 47 is secured to or held by the first HME housing portion 30 while the second bypass housing 45 is secured to or held by the second HME housing portion 32. The first bypass housing 47 contains a first partial ramp 54 therein. The second bypass housing 45 contains a second partial ramp 52 therein.

Figure 11:
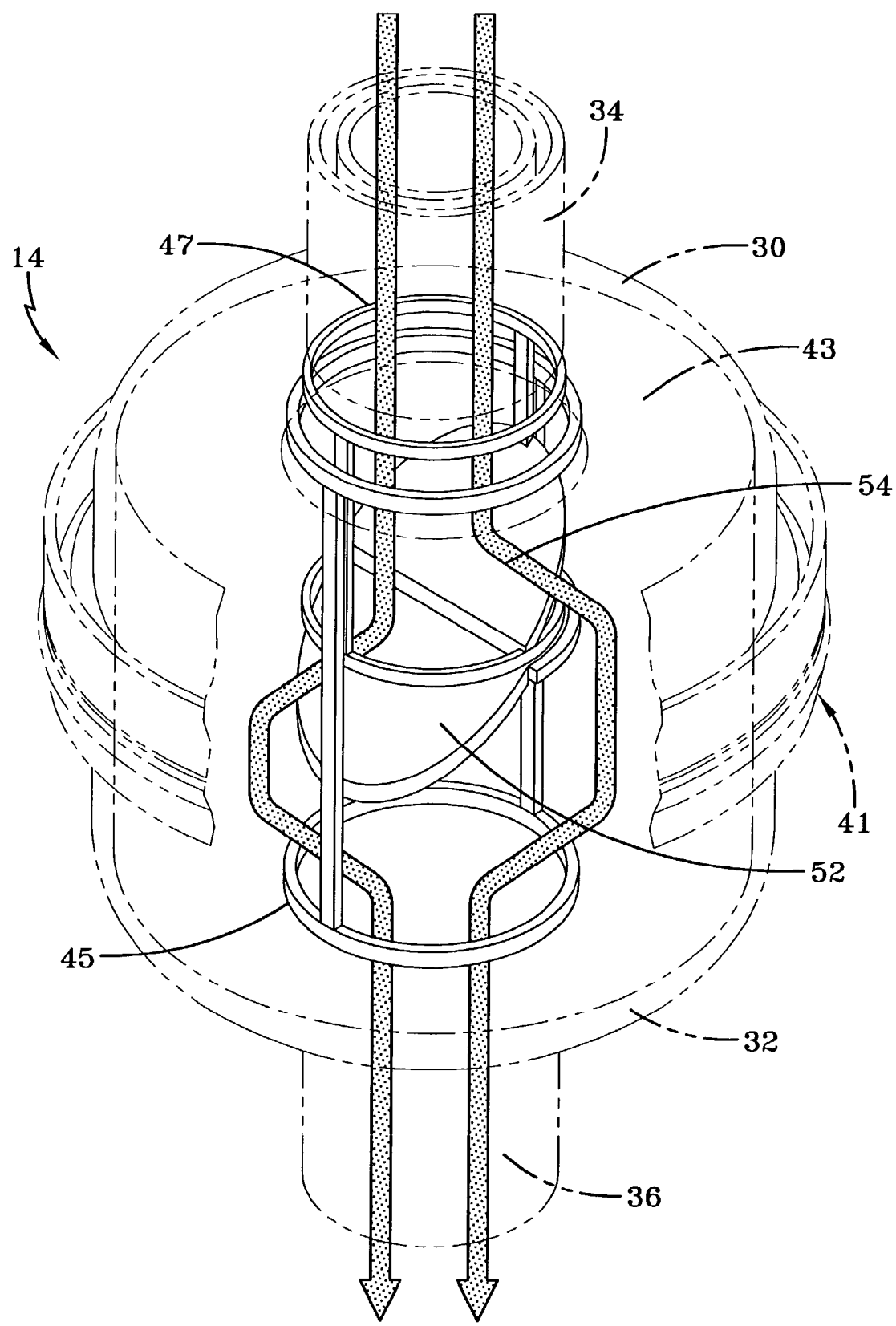
FIG. 11 is another perspective view of the HME unit showing the bypass in accordance with the present invention in phantom.

Referring to FIGS. 4, 4A and 11, an embodiment is shown that uses openings/apertures/windows 4 that allow air to flow from the inside of the bypass 46 into and through the fibrous media 43 when the ramps 52 and 54 are in the closed position. Air flow is shown as a wide arrow in the figures.

When the ramps 52 and 54 are in the open position, the openings/apertures/windows 4 will be closed thereby allowing the air to flow through the bypass 46 without touching the fibrous media 43 at all (see FIG. 4B). In essence, the arrangement in FIG. 4B with the apertures 4 closed, creates a tube through the fibrous media, thereby eliminating any portion of the flow from contacting the fibrous media 43 and thus not permitting any liquid droplets, residue or film from the flow to saturate, clog or be deposited on or in the fibrous media 43. As shown in FIGS. 4A and 4B, the ramps are rotated relative to each other to open and close bypass 46, which also allows the opening and closing of apertures 4, depending upon whether the bypass 46 (via the ramps 52 and 54) is open or closed.

As the first HME housing portion 30 rotates relative to the second HME housing portion 32, the first bypass housing 47 rotates relative to the second bypass housing 45. When the first HME housing portion 30 and second HME housing portion 32 are rotated such that the first partial ramp 54 in the first bypass housing 47 lines up with the second partial ramp 52 in the second bypass housing 45 to block the bypass 46, all air flow is diverted through the fibrous media 43 in the HME unit 14. This is shown in FIGS. 4A, 11 (see wide arrows showing air flow) and 12. In this position, the HME unit 14 of the present invention acts like a typical HME unit by absorbing moisture and heat from exhaled air from the patient and then transferring the moisture and heat to the inhaled air provided to the patient.

Figure 6:
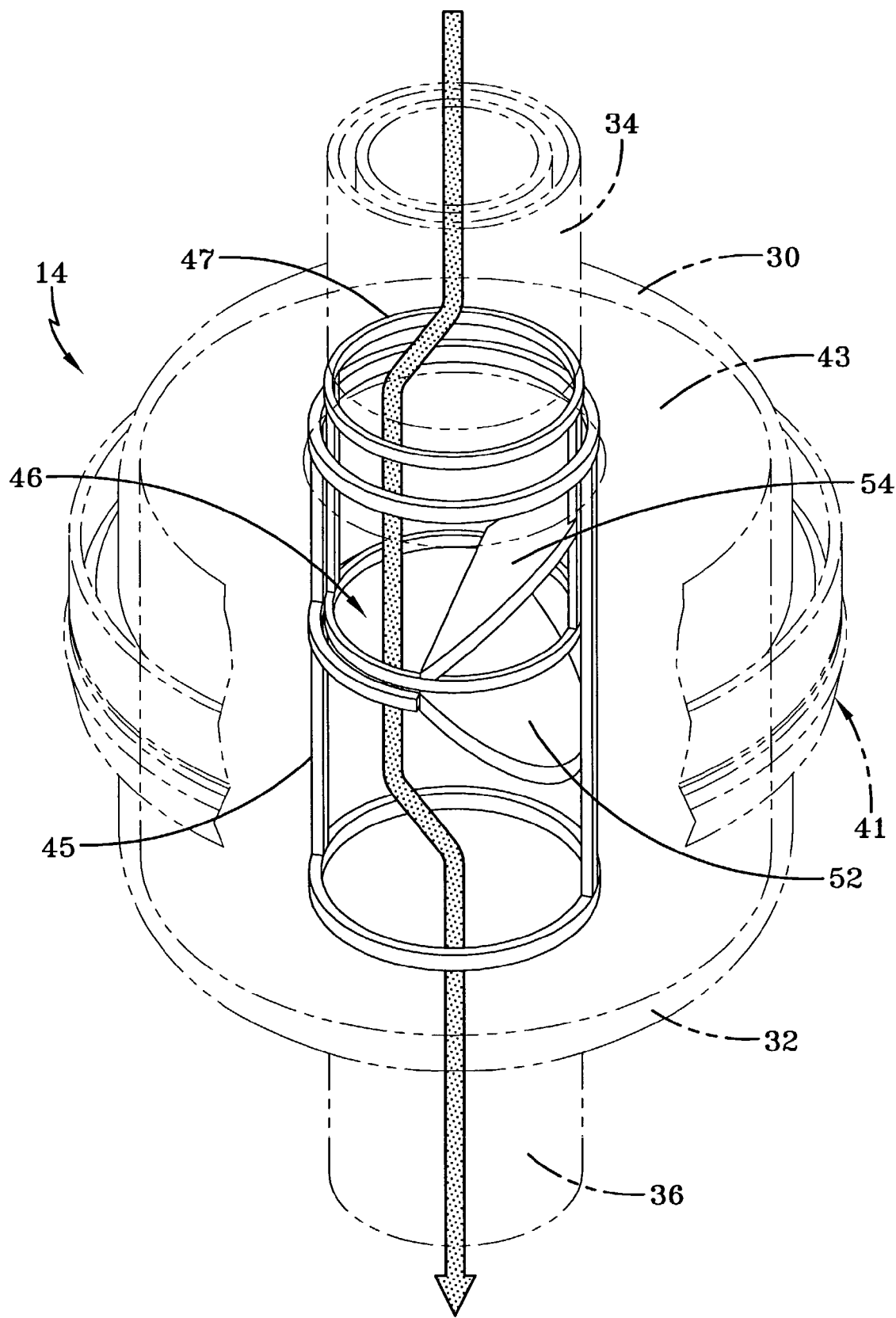
FIG. 6 is a perspective view of the HME unit showing the bypass in accordance with the present invention in phantom.
Figure 7:
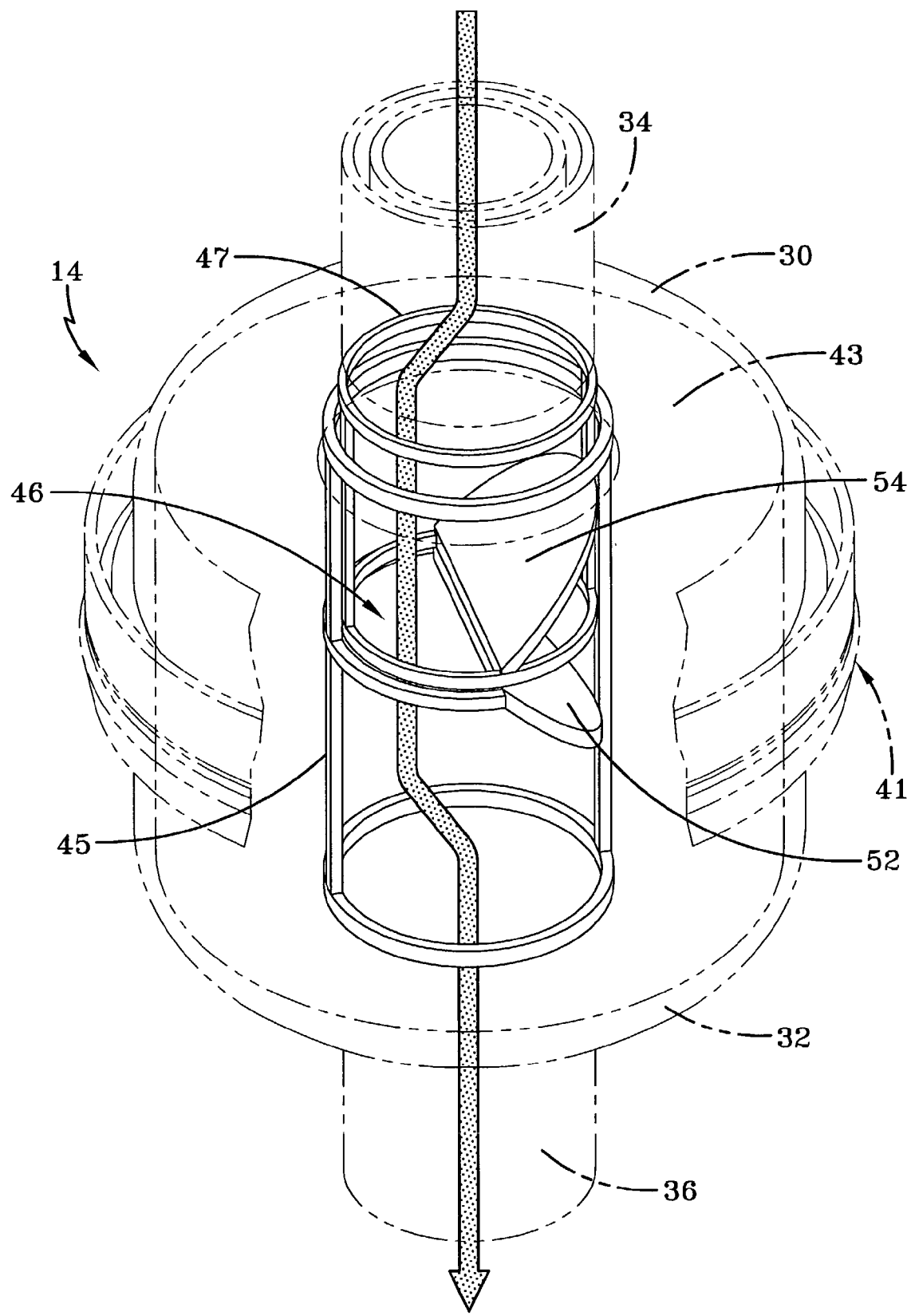
FIG. 7 is another perspective view of the HME unit showing the bypass in accordance with the present invention in phantom.
Figure 8:
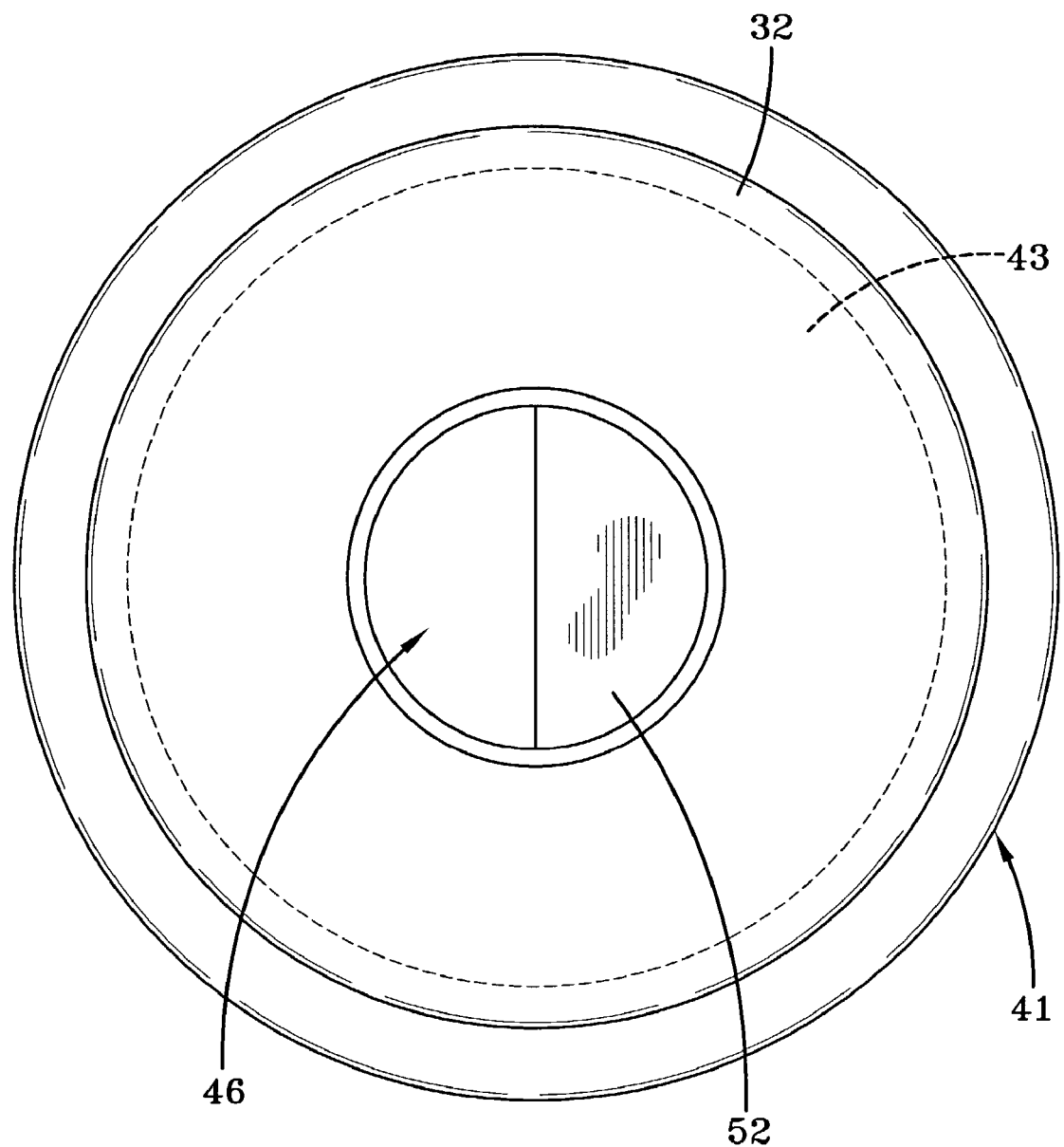
FIG. 8 is an elevated view looking through the HME unit of FIG. 6 or 7 from the distal end in accordance with the present invention.
Figure 9:
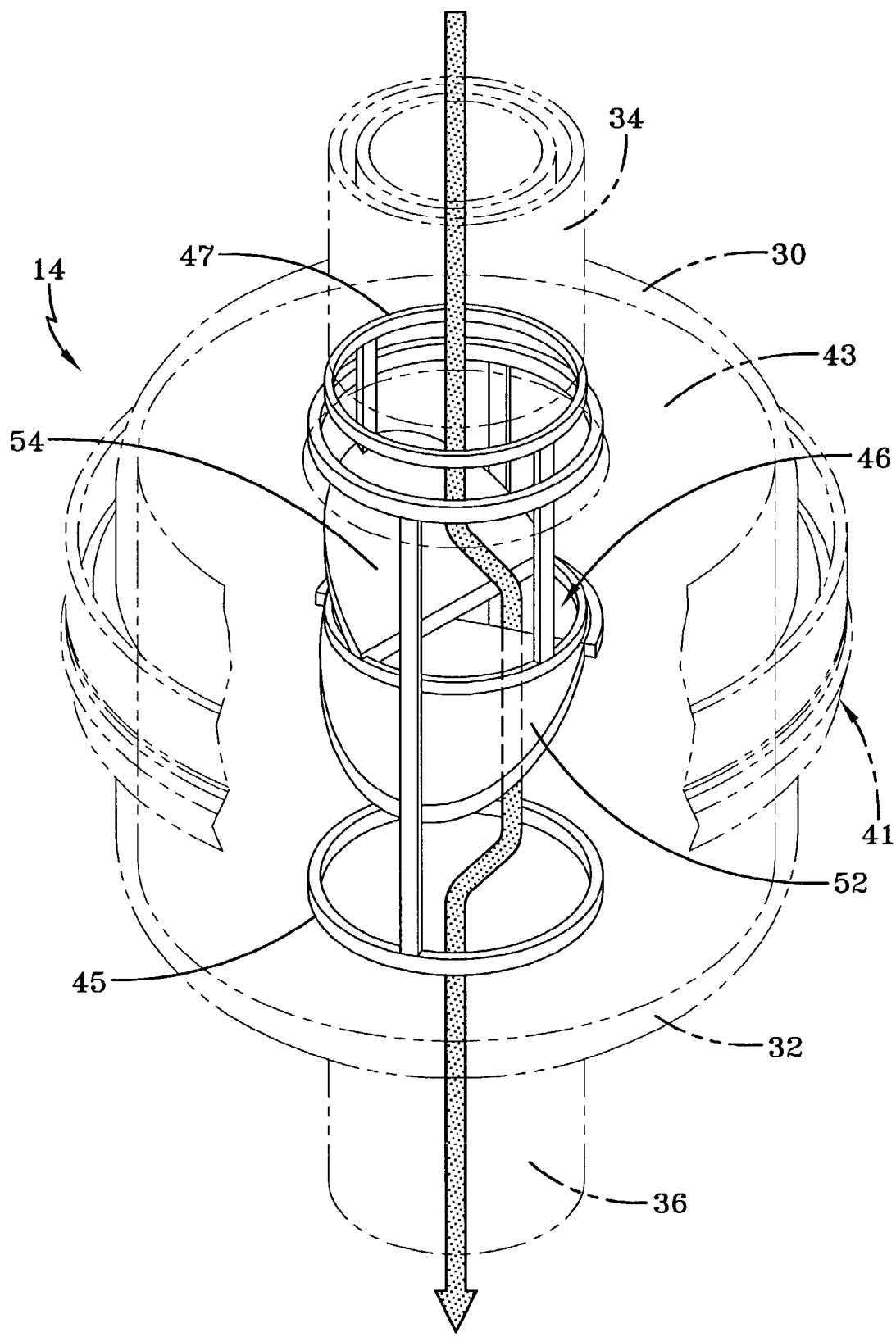
FIG. 9 is another perspective view of the HME unit showing the bypass in accordance with the present invention in phantom.

When the first HME housing portion 30 and second HME housing portion 32 are rotated such that the first partial ramp 54 of the first bypass housing 47 aligns with the second partial ramp 52 of the second bypass housing 45 in the open position, the bypass 46 is open (see wide arrows showing air flow in FIGS. 6, 7 and 9). The bypass 46 preferably would be fully open when there is a rotation of the housings of 180 degrees from the closed position. Referring to FIGS. 4B and 6–8, the open bypass 46 can be seen when the first HME housing portion 30 and the second HME housing portion 32 have been rotated in the open position. Indicia 101 can be provided on the HME unit 14 to indicate whether the bypass 46 is in the open or closed position. In addition, a detent and/or cooperating nubs 102 can be provided in the interlocking connection 41 to provide the user with a "feel" of when the bypass 46 is in the open or closed position. It is also preferable that the first HME housing portion 30 and the second HME housing portion 32 fit tight enough that vibrations will not easily move these housing portions 30 and 32 relative to each other after they are in a set position.

Once the first partial ramp 54 and the second partial ramp 55 are aligned into the open bypass position, the bypass 46 allows medication to predominately avoid the fibrous media 43 so that the nebulized air can be provided to the patient. This eliminates the possibility of the fibrous media 43 becoming clogged by the nebulized medication. Once the nebulization has been completed, the HME unit 14 of the present invention can be rotated back to the closed position, and the air provided by the ventilator is diverted through the fibrous media 43 to once again to retain moisture and heat from the exhaled air and then transfer the moisture and heat to the inhaled air.

Figure 10:
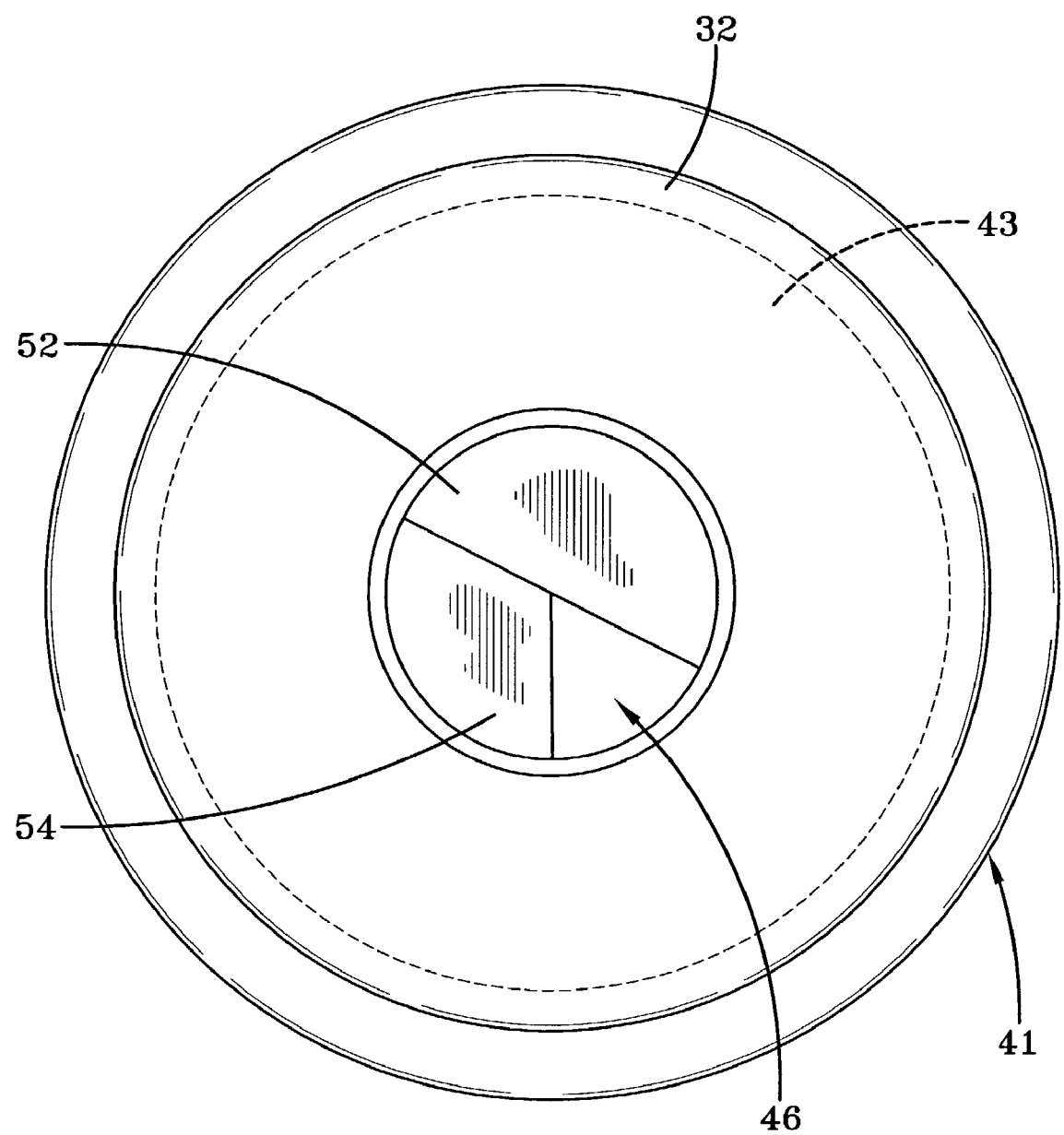
FIG. 10 is an elevated view looking through the HME unit of FIG. 9 in accordance with the present invention from the distal end.
Figure 12:
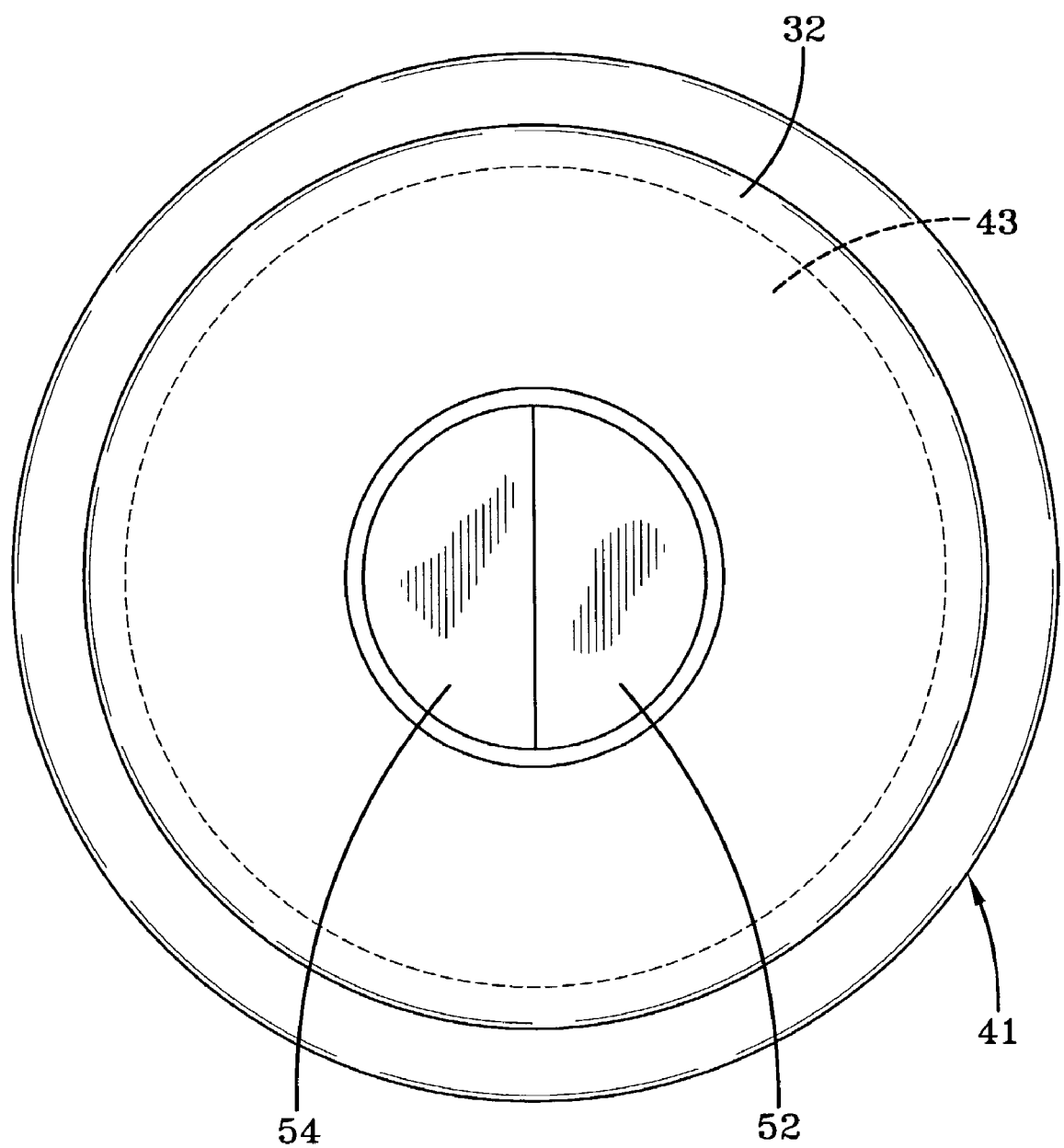
FIG. 12 is an elevated view looking through the HME unit of FIG. 11 in accordance with the present invention.

FIGS. 9 and 10 show the first partial ramp 54 and the second partial ramp 52 in a partially closed position that would still allow some air to pass through the bypass 46. In most situations, the bypass 46 of the HME unit 14 would be used in either the fully open position, as shown in FIG. 8, or in the completely closed position, as shown in FIG. 12.

Figure 15A:
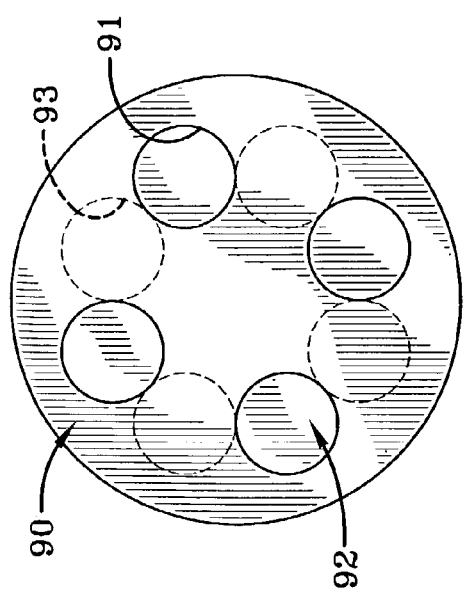
Figure 15B:
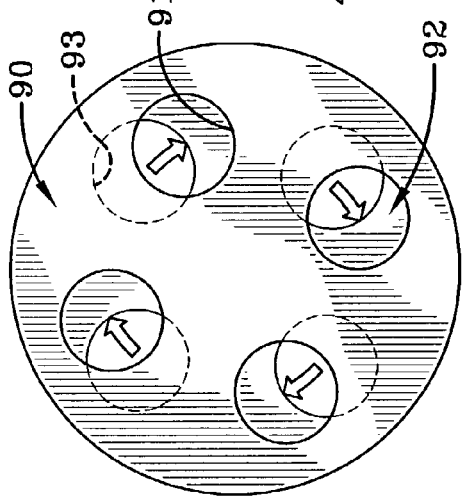
Figure 15C:
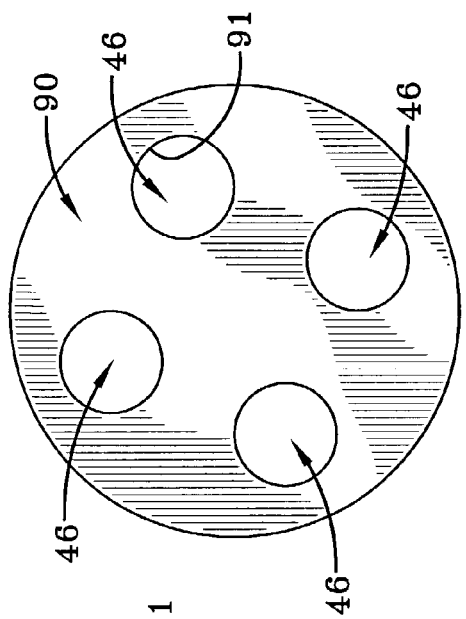
Figure 16A:
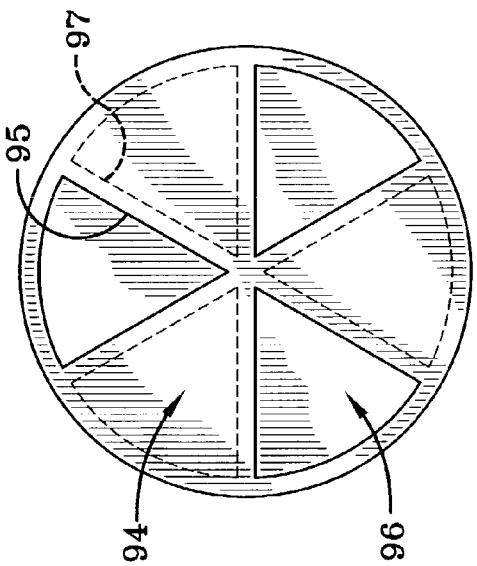
Figure 16B:
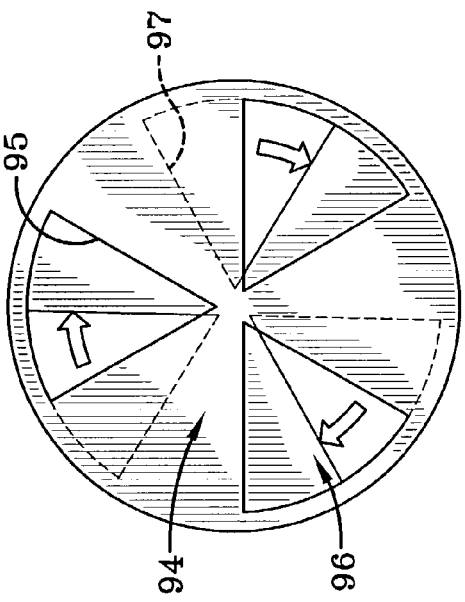
Figure 16C:
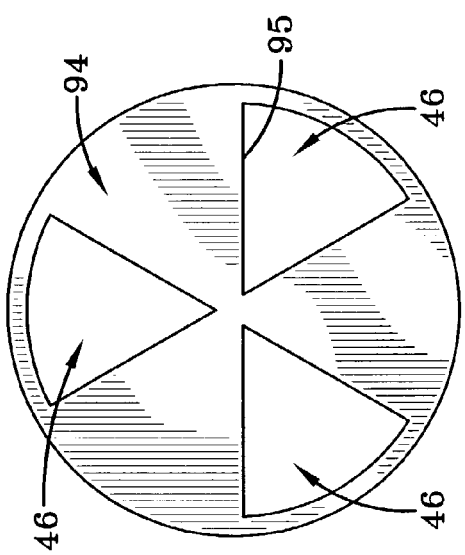

While a preferred embodiment of the HME unit 14 of the present invention contemplates use of a bypass channel 46 through the fibrous media, other types of alternative embodiments can be used which would similarly allow nebulized medication to be administered to a patient in a breathing circuit with an HME unit while maintaining a system as closed. As shown in FIGS. 15A, 15B and 15C, instead of the partial ramps 52 and 54, other internal bypass mechanisms in the bypass 46 would work, including plates 90 and 92 with apertures 91 and 93 that line up (FIG. 15C) when air is to bypass the fibrous media 43 and do not line up (FIG. 15A) when air is not to pass through bypass 46 but instead is to pass through the fibrous media 43. Similarly, as shown in FIGS. 16A, 16B and 16C, complementary pie-shaped radial apertures 95 and 97 could be used in which the apertures in the top plate 94 and the bottom plate 96 in the bypass 46 would line up (FIG. 16C) when air is to bypass the fibrous media 43 and do not line up (FIG. 16A) when air is not to pass through bypass 46 but instead is to pass through the fibrous media 43.

Figure 13A:
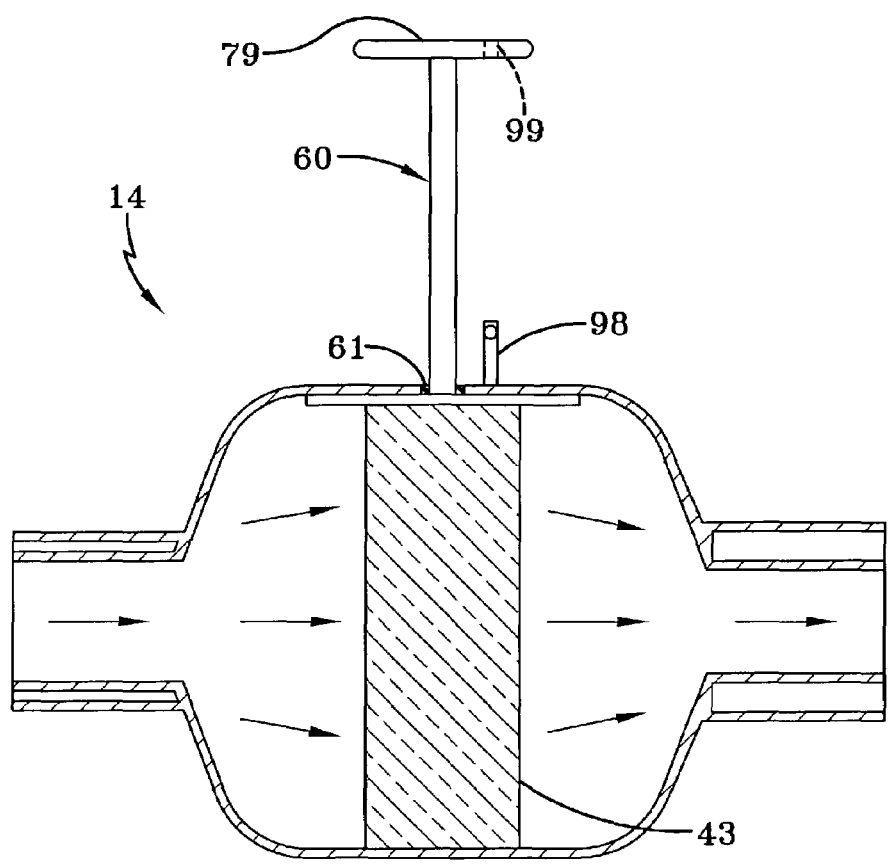
FIGS. 13A and 13B are cut away views of alternative embodiments of an HME unit in accordance with the present invention.
Figure 13B:
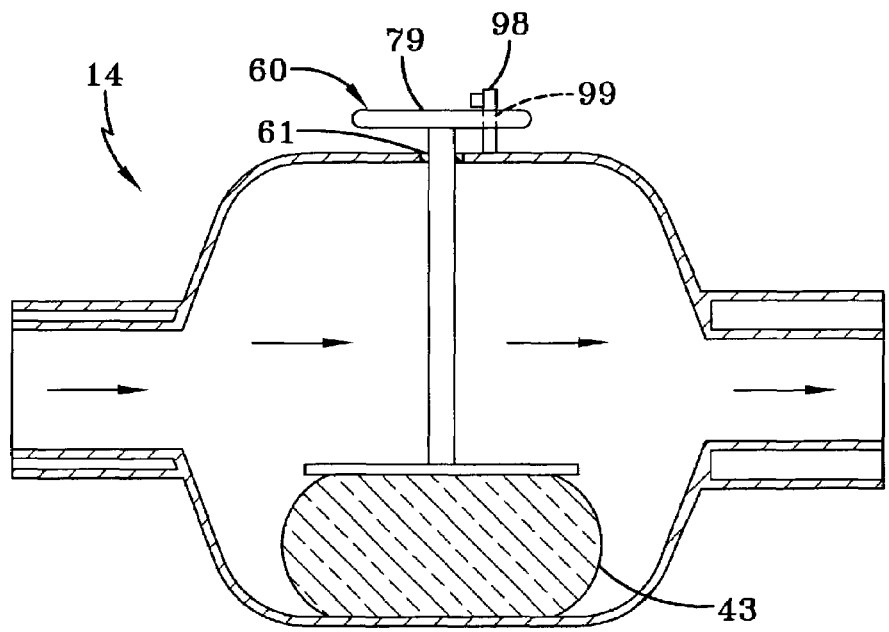

FIGS. 13A and 13B show cut away views of alternative embodiments of the HME unit 14. In this embodiment, a plunger 60 is provided through a wall of the housing of the HME unit 14. The plunger 60 can be used to "push" the fibrous media 43 out of the way of the flow path thereby providing a channel of flow for the nebulized medication that bypasses the fibrous material 43. The plunger 60 extends through a wall of the housing of the HME unit 14 and a seal 61 is provided between the plunger 60 and the housing to prevent air from outside of the housing to get into the HME unit 14. The handle 79 of the plunger 60 may have a slot 99 in it to engage an engagement member 98 of the housing of the HME unit 14 when the plunger 60 is pushed into the housing to thereby retain the plunger in a "pushed in" position while the air is flowing past the fibrous media 43. As shown in FIG. 13B, the engagement member 98 may be rotated once it is passed through slot 99 to hold the plunger 60 in the "pushed in" position.

Figure 14A:
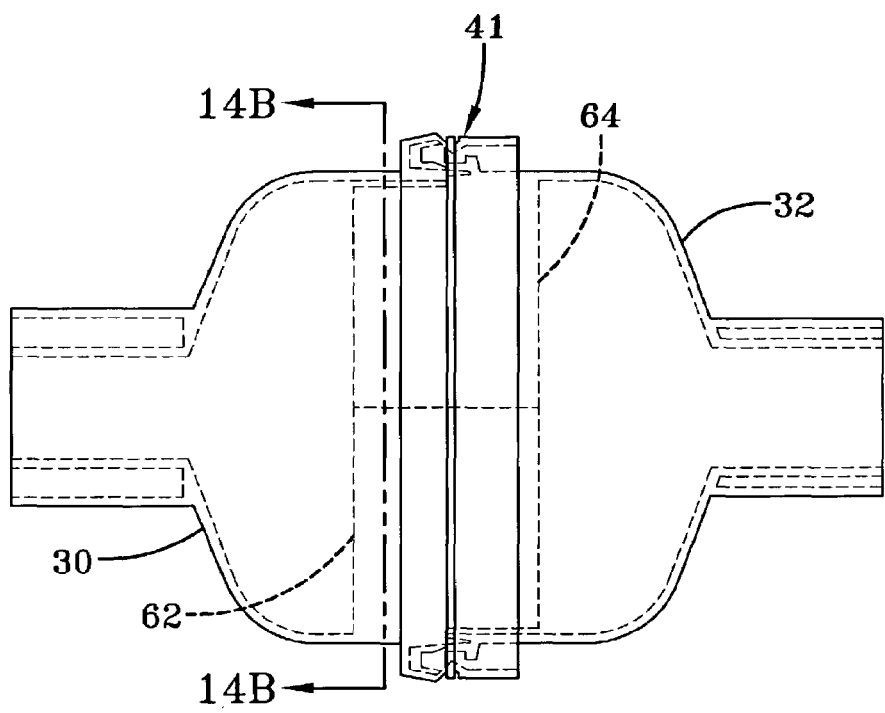
FIGS. 14A, 14B, 14C, 15A, 15B, 15C, 16A, 16B and 16C are cut away views of alternative embodiments of an HME unit in accordance with the present invention.
Figure 14B:
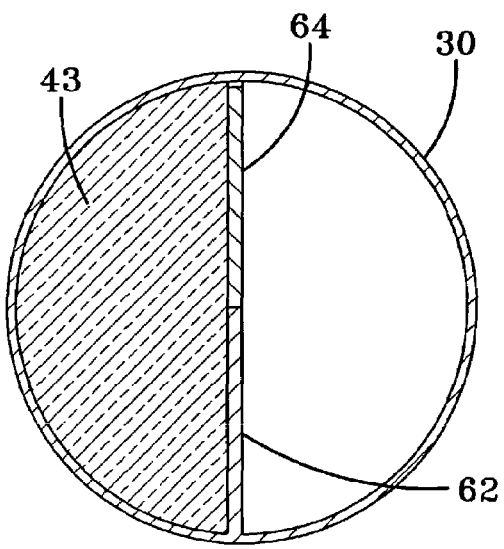
Figure 14C:
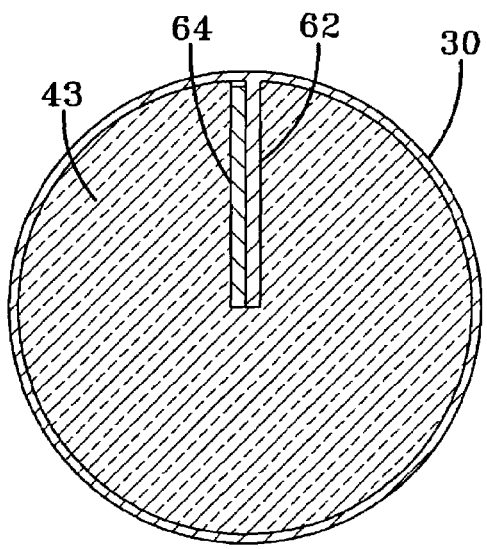

Similarly, FIGS. 14A, 14B and 14C show an alternative embodiment made in accordance with present invention. This HME unit 14 includes a first wiper 62 connected to the first HME housing portion 30 and a second wiper 64 connected to the second HME housing portion 32. The first wiper 62 and the second wiper 64 are contained in an adjacent position when the HME unit is in the closed position. Thus, in the closed position (FIG. 14C), the air is diverted through the fibrous media 43. When nebulized medicine is desired to be provided to the patient, the first HME housing portion 30 and the second HME housing portion 32 are rotated. This causes the first wiper 62 to rotate relative to the second wiper 64 thereby compressing the fibrous media 43 in between the wipers to push it out of the way of the flow path so that nebulized medication can be provided through the HME unit 14 so that very little medication touches the fibrous material 43 (FIG. 14B). The interlocking member 41 holds the first HME housing portion 30 and the second HME housing portion 32 together, but still allows rotation.

It should be understood that various changes and modifications to the preferred embodiment described herein will be apparent to those skilled in the art. For example, in addition to the preferred and alternative embodiments described therein, various other embodiment can be designed which would likewise provide for a bypass flow channel through the fibrous media. Such changes and modifications can be made without departing from the spirit and scope of the present invention and without demising its intended advantages. It is therefore intended that such changes and modifications be covered by the appended claims.

What is claimed is:

1. A heat and moisture exchange (HME) unit comprising:
a housing having a fibrous media therein that is designed to retain moisture and heat from exhaled air passing through said housing and to transfer the moisture and heat to inhaled air passing through said housing, wherein said housing includes a first HME housing portion and a second HME housing portion, the first HME housing portion being rotatably connected to the second HME housing portion; and
an internal bypass in said housing to enable air to pass through said housing without passing through the fibrous media, wherein said bypass includes a first bypass housing secured to the first HME housing portion and a second bypass housing secured to the second HME housing portion and wherein the first bypass housing contains a first partial ramp and the second bypass housing contains a second partial ramp, such that as the first HME housing portion rotates relative to the second HME housing portion, the partial ramps are positioned with respect to each other to block and unblock said bypass.

2. A heat and moisture exchange (HME) unit comprising:
a housing having a fibrous media therein that is designed to retain moisture and heat from exhaled air passing through said housing and to transfer the moisture and heat to inhaled air passing through said housing, wherein said housing includes a first HME housing portion and a second HME housing portion, the first HME housing portion being rotatably connected to the second HME housing portion; and
an internal bypass in said housing to enable air to pass through said housing without passing through the fibrous media, wherein the first HME housing portion defines a first partial ramp, the second HME housing portion defines a second partial ramp, such that as the first HME housing portion rotates relative to the second HME housing portion, the partial ramps block and unblock said bypass.

3. A heat and moisture exchange (HME) unit comprising:
a housing having a fibrous media therein that is designed to retain moisture and heat from exhaled air passing through said housing and to transfer the moisture and heat to inhaled air passing through said housing, wherein said housing includes a first HME housing portion and a second HME housing portion, the first HME housing portion being rotatably connected to the second HME housing portion; and
an internal bypass in said housing to enable air to pass though said housing without passing through the fibrous media, wherein said housing includes a first wiper connected to the first HME housing portion and to the fibrous media and a second wiper connected to the second HME housing portion and to the fibrous media, such that when the first HME housing portion and the second HME housing portion are rotated relative to each other, the first wiper rotates relative to the second wiper thereby compressing the fibrous media therebetween, which enables air to pass through said housing without passing through the fibrous media.

4. A heat and moisture exchange (HME) unit comprising:
a housing having a fibrous media therein that is designed to retain moisture and heat from exhaled air passing through said housing and to transfer the moisture and heat to inhaled air passing through said housing, wherein said housing includes a first HME housing portion and a second HME housing portion, the first HME housing portion being rotatably connected to the second HME housing portion; and
an internal bypass in said housing to enable air to pass through said housing without passing through the fibrous media, wherein said bypass includes a first bypass housing secured to the first HME housing portion and a second bypass housing secured to the second HME housing portion, such that as the first HME housing portion rotates relative to the second HME housing portion, the first bypass housing rotates relative to the second bypass housing to block and unblock said bypass, wherein said first and second bypass housings have apertures that are aligned when said bypass is blocked to allow air to flow through the apertures and through the fibrous media.

5. The heat and moisture exchange unit of claim 4, wherein the apertures are not aligned when said bypass is open to allow air to flow through said bypass without touching the fibrous media.

6. A heat and moisture exchange (HME) unit comprising:
a housing having a fibrous media therein that is designed to retain moisture and heat from exhaled air passing through said housing and to transfer the moisture and heat to inhaled air passing through said housing, wherein said housing includes a first HME housing portion and a second HME housing portion, the first HME housing portion being rotatably connected to the second HME housing portion; and
an internal bypass in said housing to enable air to pass through said housing without passing through the fibrous media, wherein said bypass includes a first bypass housing secured to the first HME housing portion and a second bypass housing secured to the second HME housing portion and wherein the first bypass housing contains a first plate having one or more apertures therethrough and the second bypass housing contains a second plate having one or more apertures therethrough, such that as the first HME housing portion rotates relative to the second HME housing portion, the apertures in the first and second plates are positioned with respect to each other to block and unblock said bypass.

7. A breathing circuit comprising:
(a) a heat and moisture exchange (HME) unit including:
a housing having a fibrous media therein that is designed to retain moisture and heat from exhaled air passing through said housing and to transfer the moisture and heat to inhaled air passing through said housing, wherein said housing includes a first HME housing portion and a second HME housing portion, the first HME housing portion being rotatably connected to the second HME housing portion; and
an internal bypass in said housing to enable air to pass through said housing without passing through the fibrous media, wherein said bypass includes a first bypass housing secured to the first HME housing portion and a second bypass housing secured to the second HME housing portion and wherein the first bypass housing contains a first partial ramp and the second bypass housing contains a second partial ramp, such that as the first HME housing portion rotates relative to the second HME housing portion, the partial ramps are positioned with respect to each other to block and unblock said bypass;

(b) a medical treatment device; and
(c) a ventilator,
wherein said ventilator, said medical treatment device and said heat and moisture exchange unit are connected in a closed system.

8. The breathing circuit of claim 7, wherein said medical treatment device is a nebulizer or a metered dose inhaler.

9. A breathing circuit comprising:
(a) a heat and moisture exchange (HME) unit including:
a housing having a fibrous media therein that is designed to retain moisture and heat from exhaled air passing through said housing and to transfer the moisture and heat to inhaled air passing through said housing, wherein said housing includes a first HME housing portion and a second HME housing portion, the first HME housing portion being rotatably connected to the second HME housing portion;
an internal bypass in said housing to enable air to pass through said housing without passing through the fibrous media, wherein said housing includes a first wiper connected to the first HME housing portion and to the fibrous media and a second wiper connected to the second HME housing portion and to the fibrous media, such that when the first HME housing portion and the second HME housing portion are rotated relative to each other, the first wiper rotates relative to the second wiper thereby compressing the fibrous media therebetween, which enables air to pass through said housing without passing through the fibrous media;
(b) a medical treatment device; and
(c) a ventilator,
wherein said ventilator, said medical treatment device and said heat and moisture exchange unit are connected in a closed system.

10. A breathing circuit comprising:
(a) a heat and moisture exchange (HME) unit comprising:
a housing having a fibrous media therein that is designed to retain moisture and heat from exhaled air passing through said housing and to transfer the moisture and heat to inhaled air passing through said housing, wherein said housing includes a first HME housing portion and a second HME housing portion, the first HME housing portion being rotatably connected to the second HME housing portion; and
an internal bypass in said housing to enable air to pass through said housing without passing through the fibrous media, wherein said bypass includes a first bypass housing secured to the first HME housing portion and a second bypass housing secured to the second HME housing portion, such that as the first HME housing portion rotates relative to the second HME housing portion, the first bypass housing rotates relative to the second bypass housing to block and unblock said bypass, wherein said first and second bypass housings have apertures that are aligned when said bypass is blocked to allow air to flow through the apertures and through the fibrous media;
(b) a medical treatment device; and
(c) a ventilator,
wherein said ventilator, said medical treatment device and said heat moisture exchange unit are connected in a closed system.

11. The breathing circuit of claim 10, wherein the apertures are not aligned when said bypass is open to allow air to flow through the bypass without touching the fibrous media.

12. A breathing circuit comprising:
(a) a heat and moisture exchange (HME) unit comprising:
a housing having a fibrous media therein that is designed to retain moisture and heat from exhaled air passing through said housing and to transfer the moisture and heat to inhaled air passing through said housing, wherein said housing includes a first HME housing portion and a second HME housing portion, the first HME housing portion being rotatably connected to the second HME housing portion;
an internal bypass in said housing to enable air to pass through said housing without passing through the fibrous media, wherein said bypass includes a first bypass housing secured to the first HME housing portion and a second bypass housing secured to the second HME housing portion and wherein the first bypass housing contains a first plate having one or more apertures therethrough and the second bypass housing contains a second plate having one or more apertures therethrough, such that as the first HME housing portion rotates relative to the second HME housing portion, the apertures in the first and second plates are positioned with respect to each other to block and unblock said bypass;
(b) a medical treatment device; and
(c) a ventilator,
wherein said ventilator, said medical treatment device and said heat and moisture exchange unit are connected in a closed system.

* * * * *